United States Patent
Zhou et al.

(10) Patent No.: US 10,482,600 B2
(45) Date of Patent: Nov. 19, 2019

(54) CROSS-DOMAIN IMAGE ANALYSIS AND CROSS-DOMAIN IMAGE SYNTHESIS USING DEEP IMAGE-TO-IMAGE NETWORKS AND ADVERSARIAL NETWORKS

(71) Applicant: Siemens Healthcare GmbH, Erlangen (DE)

(72) Inventors: Shaohua Kevin Zhou, Plainsboro, NJ (US); Shun Miao, Princeton, NJ (US); Rui Liao, West Windsor Township, NJ (US); Ahmet Tuysuzoglu, Franklin Park, NJ (US); Yefeng Zheng, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 114 days.

(21) Appl. No.: 15/872,408

(22) Filed: Jan. 16, 2018

(65) Prior Publication Data
US 2019/0220977 A1   Jul. 18, 2019

(51) Int. Cl.
*G06K 9/00*   (2006.01)
*G06T 7/00*   (2017.01)
(Continued)

(52) U.S. Cl.
CPC .......... *G06T 7/0014* (2013.01); *G06K 9/6256* (2013.01); *G06K 9/6267* (2013.01);
(Continued)

(58) Field of Classification Search
CPC . G06T 2207/20081; G06T 2207/20084; G06T 7/0014; G06T 2210/52;
(Continued)

(56) References Cited

U.S. PATENT DOCUMENTS 8,235,726 B2   8/2012 Hostettler et al.
8,241,041 B2   8/2012 Hostettler et al.
(Continued)

OTHER PUBLICATIONS

Yang, Dong, et al. "Automatic vertebra labeling in large-scale 3D CT using deep image-to-image network with message passing and sparsity regularization." International Conference on Information Processing in Medical Imaging. Springer, Cham, 2017. (Year: 2017).*

(Continued)

*Primary Examiner* — Li Liu

(57) ABSTRACT

Methods and apparatus for cross-domain medical image analysis and cross-domain medical image synthesis using deep image-to-image networks and adversarial networks are disclosed. In a method for cross-domain medical image analysis a medical image of a patient from a first domain is received. The medical image is input to a first encoder of a cross-domain deep image-to-image network (DI2IN) that includes the first encoder for the first domain, a second encoder for a second domain, and a decoder. The first encoder converts the medical image to a feature map and the decoder generates an output image that provides a result of a medical image analysis task from the feature map. The first encoder and the second encoder are trained together at least in part based on a similarity of feature maps generated by the first encoder from training images from the first domain and feature maps generated by the second encoder from training images from the second domain, and the decoder is trained to generate output images from feature maps generated by the first encoder or the second encoder.

13 Claims, 10 Drawing Sheets

(51) Int. Cl.
*G06N 3/04* (2006.01)
*G06N 3/08* (2006.01)
*G16H 30/40* (2018.01)
*G06K 9/62* (2006.01)
*G06T 5/50* (2006.01)

(52) U.S. Cl.
CPC ......... *G06N 3/0454* (2013.01); *G06N 3/0472* (2013.01); *G06N 3/084* (2013.01); *G06T 5/50* (2013.01); *G16H 30/40* (2018.01); *G06T 2207/10081* (2013.01); *G06T 2207/10088* (2013.01); *G06T 2207/10132* (2013.01); *G06T 2207/20081* (2013.01); *G06T 2207/20084* (2013.01); *G06T 2207/30056* (2013.01); *G06T 2210/41* (2013.01); *G06T 2210/52* (2013.01)

(58) Field of Classification Search
CPC .. G06N 3/0454; A61B 5/0035; G06K 9/6267; G06K 9/66; G06K 2209/05
See application file for complete search history.

(56) References Cited

U.S. PATENT DOCUMENTS

| | | | |
|---|---|---|---|
| 8,700,552 | B2 | 4/2014 | Yu et al. |
| 8,761,471 | B2 | 6/2014 | Ozawa et al. |
| 9,275,308 | B2 | 3/2016 | Szegedy et al. |
| 9,373,059 | B1 | 6/2016 | Heifets et al. |
| 9,760,807 | B2 | 9/2017 | Zhou et al. |
| 2008/0037851 | A1 | 2/2008 | Takayama |
| 2008/0312884 | A1 | 12/2008 | Hostettler et al. |
| 2009/0046912 | A1 | 2/2009 | Hostettler et al. |
| 2012/0148139 | A1 | 6/2012 | Ozawa et al. |
| 2013/0035583 | A1 | 2/2013 | Park et al. |
| 2013/0138436 | A1 | 5/2013 | Yu et al. |
| 2013/0138589 | A1 | 5/2013 | Yu et al. |
| 2013/0259336 | A1 | 10/2013 | Wakai |
| 2013/0342668 | A1 | 12/2013 | Kasumi et al. |
| 2015/0112182 | A1 | 4/2015 | Sharma et al. |
| 2015/0125049 | A1 | 5/2015 | Taigman et al. |
| 2015/0161987 | A1 | 6/2015 | Horesh et al. |
| 2015/0161988 | A1 | 6/2015 | Dognin et al. |
| 2015/0170002 | A1 | 6/2015 | Szegedy et al. |
| 2015/0238148 | A1 | 8/2015 | Georgescu et al. |
| 2016/0063359 | A1 | 3/2016 | Szegedy et al. |
| 2016/0093048 | A1 | 3/2016 | Cheng et al. |
| 2016/0140424 | A1 | 5/2016 | Wang et al. |
| 2016/0174902 | A1 | 6/2016 | Georgescu et al. |
| 2016/0180195 | A1 | 6/2016 | Martinson et al. |
| 2016/0210749 | A1 | 7/2016 | Nguyen et al. |
| 2016/0328643 | A1 | 11/2016 | Liu et al. |
| 2017/0200067 | A1 | 7/2017 | Zhou et al. |
| 2017/0277981 | A1 | 9/2017 | Zhou et al. |
| 2017/0316286 | A1 | 11/2017 | Szegedy et al. |
| 2018/0116620 | A1* | 5/2018 | Chen ........................ A61B 6/03 |
| 2018/0225823 | A1* | 8/2018 | Zhou ..................... G06K 9/6267 |
| 2018/0260951 | A1* | 9/2018 | Yang ..................... G06N 3/0445 |
| 2018/0260957 | A1* | 9/2018 | Yang ..................... G06T 7/0012 |
| 2018/0271460 | A1* | 9/2018 | Geiger ................. A61B 5/0035 |
| 2019/0057521 | A1* | 2/2019 | Teixeira ............... G06K 9/6262 |
| 2019/0205606 | A1* | 7/2019 | Zhou ..................... G06N 3/0445 |
| 2019/0216409 | A1* | 7/2019 | Zhou ..................... G06T 11/003 |

OTHER PUBLICATIONS

Sela, Matan, Elad Richardson, and Ron Kimmel. "Unrestricted facial geometry reconstruction using image-to-image translation." Proceedings of the IEEE International Conference on Computer Vision. 2017. (Year: 2017).*

Liu, Ming-Yu, and Oncel Tuzel. "Coupled generative adversarial networks." Advances in neural information processing systems. 2016. (Year: 2016).*

Makhzani, Alireza, et al. "Adversarial autoencoders." arXiv preprint arXiv:1511.05644 (2015). (Year: 2015).*

Springenberg, Jost Tobias. "Unsupervised and semi-supervised learning with categorical generative adversarial networks." arXiv preprint arXiv:1511.06390 (2015). (Year: 2015).*

Goodfellow et al., "Generative Adversarial Nets"; Universite of Montreal, Montreal, QC; Jun. 10, 2014; pp. 1-9.

Dong Yang et al: "Automatic Liver Segmentation Using an Adversarial Image-to-Image Network"; Arxiv.Org, Cornell University Library, 201 Olin Library Cornell University Ithaca, NY 14853.

Phillip Isola et al: "Image-to-Image Translation with Conditional Adversarial Networks"; pp. 5967-5976; Berkeley AI Research (BAIR) Laboratory, UC Berkeley (2017).

Goodfellow, Ian J. et al.,"Generative Adversarial Networks", arXiv:1406.2661v1 of Jun. 10, 2014; XP055549980; pp:1-9.

Partial European Search Report dated Jun. 6, 2019 in corresponding European Application No. 19151565.9.

* cited by examiner

CROSS-DOMAIN IMAGE ANALYSIS AND CROSS-DOMAIN IMAGE SYNTHESIS USING DEEP IMAGE-TO-IMAGE NETWORKS AND ADVERSARIAL NETWORKS

BACKGROUND OF THE INVENTION

The present invention relates to cross-domain medical image analysis and cross-domain synthesis of medical images, and more particularly, to cross-domain medical image analysis and cross-domain medical image synthesis using deep learning networks.

A multitude of imaging modalities, such as computed tomography (CT), diffuser tensor imaging (DTI), T1-weighted magnetic resonance imaging (MRI), T2-weighted MRI, ultrasound, X-ray, positron emission tomography (PET), etc., can be used for medical image analysis of a of a patient. Each of these imaging modalities captures different characteristics of the underlying anatomy and the relationship between any two modalities is highly nonlinear. These different imaging techniques provide physicians with varied tools and information for making accurate diagnoses. However, sensor heterogeneity creates challenges for developing effective automatic image analysis platforms. In particular, algorithms that work well on one modality can be rendered useless on data collected from a different type of scanner.

In many practical medical image analysis problems, a situation is often encountered in which medical image data available for training, for example for machine learning based anatomical object detection, has a different distribution or representation than the medical image data given during testing due to modality heterogeneity or domain variation. Due to variations in the image characteristics across modalities, medical image analyses algorithms trained with data from one modality may not work well when applied to medical image data from a different modality. One way to address this issue is to collect large amounts of training data from each imaging modality. However, this solution is impractical since collecting medical images is often time consuming and expensive.

Cross-modal synthesis generates medical images in a desired target modality from given source modality images. The ability to synthesize medical images without actual acquisition has many potential applications, such as atlas construction, virtual enhancement, multi-modal registration, and segmentation. Various approaches for cross-modal synthesis have been proposed, but such approaches are typically tailored to specific applications or based on various heuristics.

BRIEF SUMMARY OF THE INVENTION

The present invention provides a methods and systems for automated computer-based cross-domain medical image analysis and cross-domain synthesis of medical images.

In one embodiment of the present invention, a method for automatically performing cross-domain based medical image analysis on a medical image of a patient comprises: receiving a medical image of a patient from a first domain; inputting the medical image of the patient to a first encoder of a cross-domain deep image-to-image network including the first encoder for the first domain, a second encoder for a second domain, and a decoder; and automatically generating an output image that provides a result of a target medical image analysis task on the input medical image using the cross-domain deep image-to-image network, by the first encoder converting the input medical image from the first domain to a feature map and the decoder generating the output image from the feature map generated by the first encoder. The first encoder for the first domain is trained together with the second encoder for the second domain at least in part based on a similarity of feature maps generated by the first encoder from training input images from the first domain and feature maps generated by the second encoder from training input images from the second domain. The decoder is trained to generate output images from the feature maps generated by the first encoder and the feature maps generated by the second encoder.

In another embodiment of the present invention, a method for training deep neural networks for cross-domain bilateral medical image synthesis comprises: receiving a first set of training images of a first domain and a second set of training images in a second domain; and training, based on the first set of training images of the first domain and the second set of training images of the second domain, a bilateral generative adversarial network including a first generator network for generating a synthesized medical image of the second domain from an input medical image of the first domain, a second generator network for generating a synthesized medical image of the first domain from an input medical image of the second domain, a first discriminator network for distinguishing between real training images of the first domain and synthesized medical images of the first domain generated by the second generator network from the training images of the second domain, and a second discriminator network for distinguishing between real training images of the second domain and synthesized medical images of the second domain generated by the first generator network from the training images of the first domain. The training of the bilateral generative adversarial network rewards consistency between the training images of the first domain and synthesized images of the first domain generated by the second generator network from synthesized images of the second domain generated by the first generator network from the training images of the first domain, and consistency between the training images of the second domain and synthesized images of the second domain generated by the first generator network from synthesized images of the first domain generated by the second generator network from the training images of the second domain.

These and other advantages of the invention will be apparent to those of ordinary skill in the art by reference to the following detailed description and the accompanying drawings.

DETAILED DESCRIPTION

Figure 1:
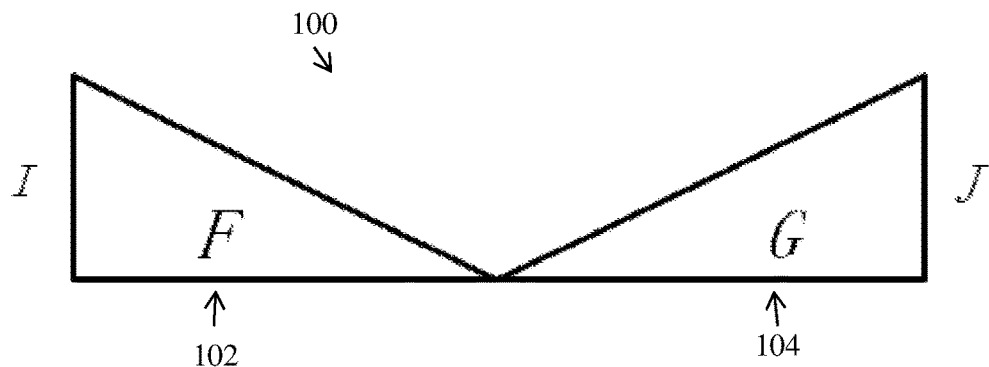
FIG. 1 illustrates a deep image-to-image network (DI2IN) for medical image analysis according to an embodiment of the present invention.

The present invention relates to a methods and systems for automated computer-based cross-domain medical image analysis and cross-domain medical image synthesis. Embodiments of the present invention are described herein to give a visual understanding of the cross-domain medical image analysis and cross-domain medical image synthesis methods. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Medical images can be acquired using different types of imaging devices, such as ultrasound, computed tomography (CT), and magnetic resonance imaging (MRI) image acquisition devices. Analysis of such medical images thus can benefit from leveraging shared knowledge from multiple domains. For example, consider the medical image analysis task of segmented target anatomical structures from medical images. The same anatomical structure, e.g., the liver, appearing in CT and MRI images for the same patient shares the same morphology though its appearance is different. Designing two independent segmentation pipelines, one for CT and the other for MRI, is suboptimal. Embodiments of the present invention provide a machine learning based method for cross-domain image analysis. In an advantageous embodiment of the present invention, a deep image-to-image network and adversarial network are used to train together deep neural networks to perform medical image analysis tasks for medical images from different domains, such that knowledge from one domain can improve the performance of the medical image analysis tasks in another domain. A practical benefit of the method described herein arises when one domain (e.g., a source domain) has a sizeable amount of annotated datasets and another domain (e.g., a target domain) has a limited amount of annotated images, or in the extreme, no annotated images. Under such circumstances, cross-domain image analysis can lead to a more effective medical image analysis in the target domain.

As used herein, medical images from different "domains" refer to medical images from different medical imaging modalities, such as CT, MRI, ultrasound, etc., as well as medical across an image domain, such MR images with different protocols (e.g., T1 and T2), contrast CT images and non-contrast CT images, CT images captured with low kV and CT images captured with high kV, or low and high resolution medical images. That is, a "first domain" and "second domain" may be completely different medical imaging modalities or different image domains or protocols within the same overall imaging modality.

A family of model estimation tasks can be formulated within a deep image-to-image network (DI2IN) learning framework, which is fully convolutional. In a DI2IN, the input is an image (or multiple images) and the output is also an image of the same grid size that represents the result of the target medical image analysis task. This framework can be applied to perform many medical image analysis tasks. For example, for landmark detection, an image with a Gaussian blob around the target landmark can be used to represent a landmark. For image segmentation, the mask image is already in the image representation format. As described in U.S. Pat. No. 9,760,807, entitled "Deep Image-to-Image Network Learning for Medical Image Analysis," which is incorporated herein in its entirety by reference, various medical image analysis tasks such as detection, segmentation, registration, denoising, and cross-modality synthesis can be formulated in a DI2IN framework.

FIG. 1 illustrates a deep image-to-image network (DI2IN) 100 for medical image analysis according to an embodiment of the present invention. As shown in FIG. 1, the DI2IN 100 inputs an input image I and outputs an output image J. The DI2IN 100 includes an encoding network (or encoder) F 102, which depicts the input image I from low-level to high-level representations, and a decoding network (or decoder) G 104, which converts the high-level representation back to a pixel-level semantic representation to generate the output image J. This can be expressed as:

$$J = G(F(I)). \qquad (1)$$

The encoder F 102 of the DI2IN 100 has a series of layers that code the input image I into a code (feature map) whose size is substantially less than the size of the input image I. The decoder G 104 of the DI2IN 100 has a series of layers that will then decode the code into the output image J. All the intermediate information generated in the encoder F 102 is shared with the decoder G 104, so that no information is lost in the encoding process.

Figure 2:
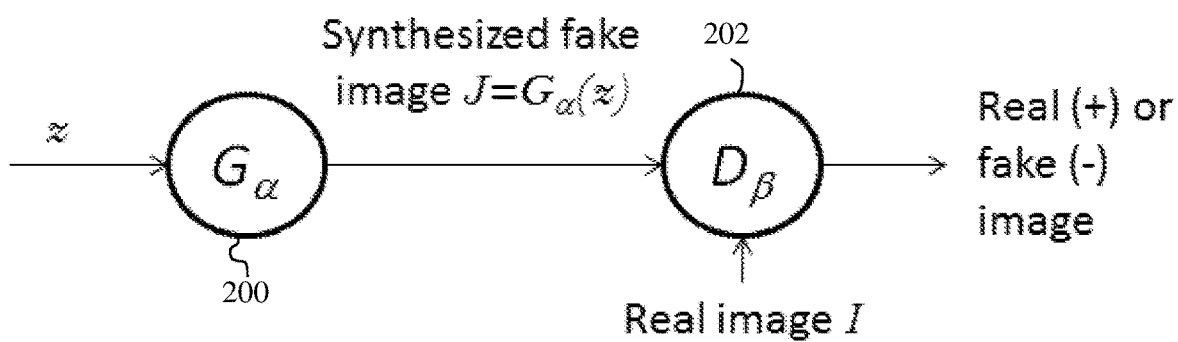
FIG. 2 illustrates a generative adversarial network for image generation.

A generative adversarial network (GAN) is a new paradigm for image generation. FIG. 2 illustrates a generative adversarial network for image generation. As shown in FIG. 2, the GAN includes two modules in the form of deep networks: a generator (or G-network) $G_\alpha$ 200 for image generation and a discriminator (or D-network) $D_\beta$ 202 for distinguishing between a real image and a synthesized image. The generator $G_\alpha$ 200 generates a synthesized image $J = G_\alpha(z)$ from some input z. The discriminator $D_\beta$ 202 inputs the synthesized image $J = G_\alpha(z)$ generated by the generator $G_\alpha$ 200 and a real image I and classifies each of these images as real or fake (synthesized). During training, the generator $G_\alpha$ 200 and the discriminator $D_\beta$ 202 together play the following minimax game:

$$\min_\alpha \max_\beta E_{I \sim p(I)}[\log(D_\beta(I))] + E_{z \sim p(z)}[\log(1 - D_\beta(J = G_\alpha(z)))], \qquad (2)$$

where $\alpha$ and $\beta$ are the parameters (weights) of the generator $G_\alpha$ 200 and discriminator $D_\beta$ 202, respectively. The generator $G_\alpha$ 200 and the discriminator $D_\beta$ 202 evolve dynamically in the sense of learning better network parameters, as long as the game is on until they reach equilibrium; that is, the synthesized image $I = G_\alpha(z)$ becomes indistinguishable (or a close to indistinguishable as possible) from the real image through the eye of the discriminator $D_B$ 202. Under such circumstances, the generator essentially generates a real image. The GAN framework enables rapid progress in synthesizing real images, but has not been applied to model estimation.

Figure 3:
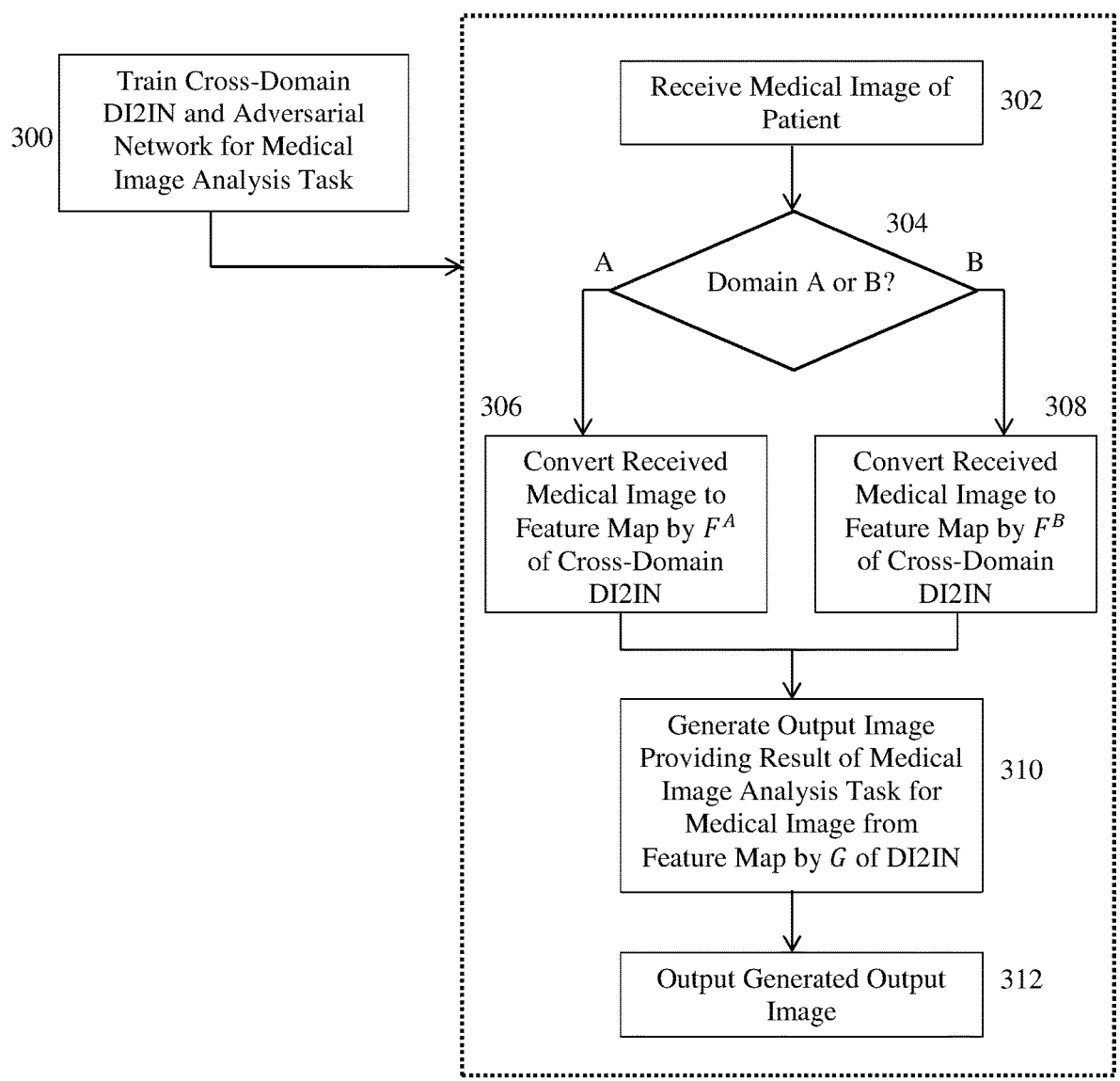
FIG. 3 illustrates a method for automatic cross-domain medical image analysis using a cross-domain deep image-to-image network.

In an advantageous embodiment, a deep image-to-image network and an adversarial network learning framework are integrated to train a cross-domain deep image-to-image network (DI2IN) for cross domain medical image analysis. FIG. 3 illustrates a method for automatic cross-domain medical image analysis using a cross-domain deep image-to-image network. The method of FIG. 3 includes a training stage (step 300) and an inference stage (steps 302-312). The training stage (step 300) is performed off-line to train a cross-domain DI2IN for a particular medical image analysis task. The inference stage (steps 302-312) performs the medical image analysis task on a newly received medical image using the trained cross-domain DI2IN resulting from the training stage. Once the cross-domain DI2IN for a particular medical image analysis task is trained in the training stage, the inference stage can be repeated for each newly received medical image(s) to perform the medical image analysis task on each newly received input medical image(s) using the trained cross-domain DI2IN.

Figure 4:
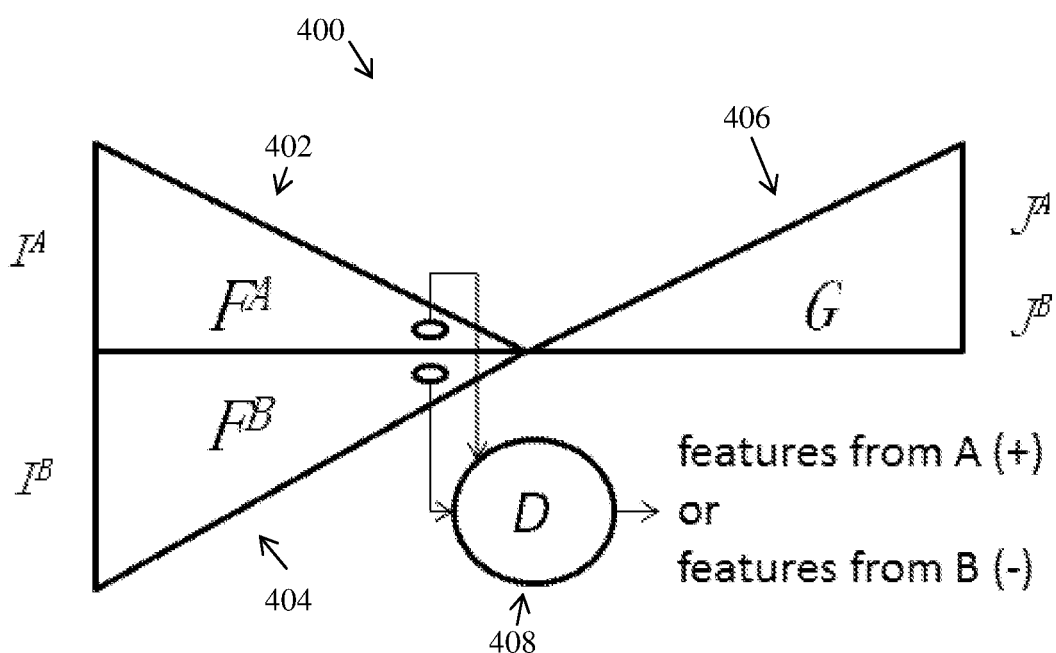
FIG. 4 illustrates a cross-domain DI2IN with an adversarial network according to an embodiment of the present invention.

At step 300, in the training stage, a cross-domain deep image-to-image network (DI2IN) and an adversarial network are trained for a medical image analysis task. FIG. 4 illustrates a cross-domain DI2IN with an adversarial network according to an embodiment of the present invention. The cross-domain DI2IN 400 of FIG. 4 is trained to perform the target medical image analysis task for two domains (A and B) of medical images. Domains A and B can be any two domains of medical images, such as different medical imaging modalities (e.g., CT and MRI) or different image domains within the same medical imaging modality (e.g., T1-weighted MRI and T2-weighted MRI). The target medical image analysis task can be any medical image analysis task, such as landmark detection, anatomical object segmentation, etc. For example, in a possible implementation, the cross-domain DI2IN 400 can be trained to perform segmentation of an organ (e.g., the liver) in both CT and MRI images.

Suppose that for two domains of interest, A and B, both domains are independent. In that case, independent DI2IN's for domains A and B are given by $J^A = G^A(F^A(I^A))$ and $J^B = G^B(F^B(I^B))$, respectively. Both the encoders and the decoders in the independent DI2IN's are separate functions. According to an advantageous embodiment of the present invention, since the same medical image analysis task is performed for both domains, we impose a constraint that the cross-domain DI2IN 400 uses the same decoder function (network) for both domains. As shown in FIG. 4, the cross-domain DI2IN 400 includes a first encoder $F^A$ 402 for a first domain (domain A), a second encoder $F^B$ 404 for a second domain (domain B), and a decoder G 406. The first encoder $F^A$ 402 converts an input image $I^A$ from domain A to a feature map that provides a high-level representation of $I^A$. The second encoder $F^B$ 404 converts an input image $I^B$ from domain B to a feature map that provides a high-level representation of $I^B$. The decoder G 406 generates an output image $J^A$ from the feature map generated from $I^A$ by the first encoder $F^A$ 402 and generates an output image $J^B$ from the feature map generated from $I^B$ by the second encoder $F^B$ 404. The training of the cross-domain DI2IN 400 aims to minimize the following error cost:

$$\min_{F^A, F^B, G} \text{err} = E_{I^A \sim p(I^A)}[C(J^A, G(F^A(I^A)))] + E_{I^B \sim p(I^B)}[C(J^B, G(F^B(I^B)))], \tag{3}$$

where $C(.,.)$ is a cost function that computes an error between a ground truth output image and an estimated output image. In an exemplary implementation, the cost function C may compute a pixel-wise (or voxel-wise for 3D images) error/distance between the estimated output image and the ground truth output image. For example, the cost function C may be implemented using a regressive or logistic function. Additional examples of cost functions that can be used to calculate the error between the ground truth and estimated output images are described in U.S. Pat. No. 9,760,807, entitled "Deep Image-to-Image Network Learning for Medical Image Analysis," which is incorporated herein in its entirety by reference.

In addition, as shown in FIG. 4, the encoders $F^A$ 402 and $F^B$ 404 and the decoder G 406 of the cross-domain DI2IN 400 are trained together with a discriminator (or D-network) D 408 as an adversarial network. The discriminator D 408 is a deep neural network that distinguishes between feature maps generated by the first encoder $F^A$ 402 from input images $I^A$ from domain A and feature maps generated by the second encoder $F^B$ 404 from input images $I^B$ from domain B. The discriminator D 408 inputs the feature maps generated by the first encoder $F^A$ 402 and the second encoder $F^B$ 404 and classifies each feature map being features from domain A (positive) or features from domain B (negative). In an exemplary implementation, the discriminator D 408 may compute a probability score for each feature map corresponding to the probability that the feature map is from domain A and classify the feature map as positive (from domain A) or negative (from domain B) based on the probability score. The adversarial network serves as a deep supervision signal, and is implemented by adding the following minimax game as part of the overall error cost function:

$$\min_{F^A, F^B, G} \{\text{err} + \max_D E_{I^A \sim p(I^A)}[\log(D(F^A(I^A)))] + E_{I^B \sim p(I^B)}[\log(1 - D(F^A(I^A)))]\}. \tag{4}$$

During training, the equilibrium is achieved in this adversarial network feature maps output by the encoders $F^A$ 402 and $F^B$ 404 of both domains from respective sets of training samples share the same distribution so that they become indistinguishable to the discriminator D 408.

Figure 5:
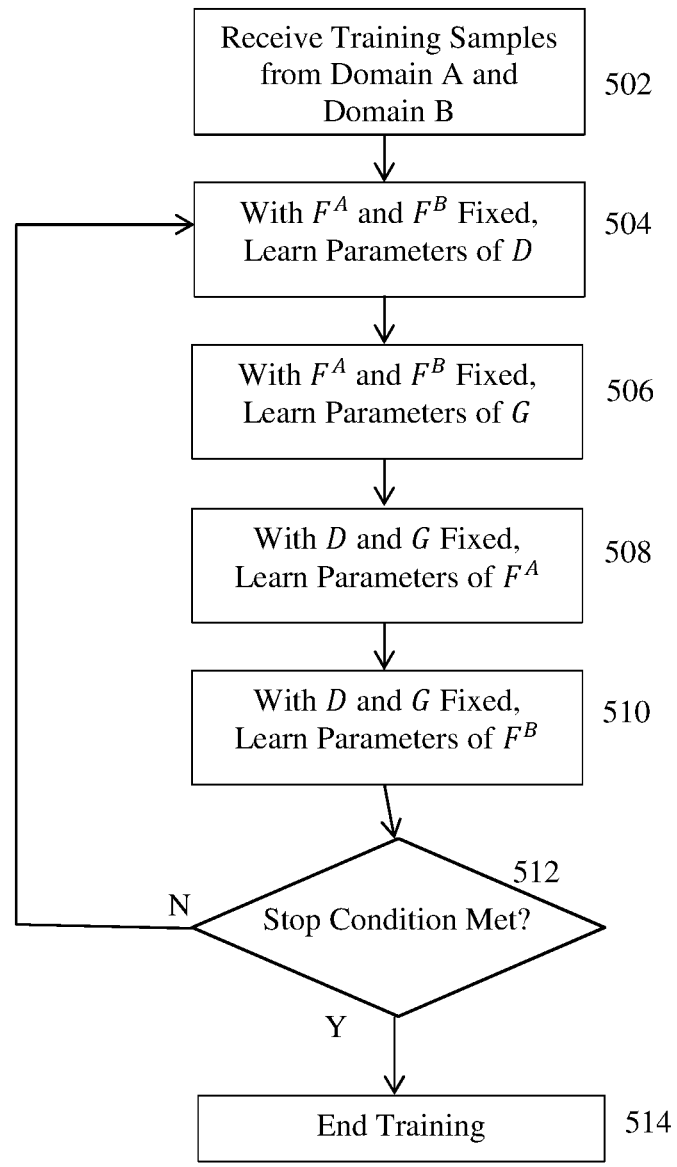
FIG. 5 illustrates a method for training the cross-domain DI2IN and adversarial network according to an embodiment of the present invention.

FIG. 5 illustrates a method for training the cross-domain DI2IN and adversarial network according to an embodiment of the present invention. The method of FIG. 5 can be used to train the cross-domain DI2IN 400 and adversarial network of FIG. 4 in order to implement step 300 of FIG. 3. At step 502, training samples from the first domain A and the second domain B are received. In particular, a first set of M training pairs $\{(I^A_m, J^A_m)\}$ from domain A and a second set of N training pairs $\{(I^B_N, J^B_n)\}$ from domain B. For each domain, each training pair includes a training input image I from that domain and a corresponding ground truth output image J that provides the results of the target medical image analysis task for the corresponding training input image I. In many cases, the set of training pairs from one domain will be much larger than the set of training pairs from the other domain (e.g., M»N). In such cases, the training of the cross-domain DI2IN 400 and adversarial network is beneficial since knowledge learned from training the encoder for the domain with the larger set of training pairs is automatically integrated into the training of the encoder for the other domain with the smaller set of training pairs.

The DI2IN framework can be used to formulate many different medical image analysis problems. In order to use the DI2IN framework to perform a particular medical image analysis task, an output image must be defined that provides the result of that medical image analysis task. For the medical image analysis task of landmark detection, each output image (in each domain) can be an image with a Gaussian-like blob surrounding each landmark. For anatomical object (e.g., organ) detection, each output image (in each domain) can be a binary mask with pixels (or voxels) equal to 1 within a bounding box surrounding the target anatomical object and equal 0 at all other pixel locations. For image segmentation, each output image (in each domain) can be a mask image whose value is 1 inside the segmented object boundary and 0 outside the segmented object boundary. For image denoising, each output image (in each domain) is a denoised image. Additional formulations for output images that can be used to provide results for various medical image analysis tasks are described in U.S. Pat. No. 9,760,807, entitled "Deep Image-to-Image Network Learning for Medical Image Analysis," which is incorporated herein in its entirety by reference.

The training input images from each domain are medical images acquired using a medical imaging modality corresponding to the domain, such as computed tomography (CT), magnetic resonance (MR), DynaCT, ultrasound, x-ray, positron emission tomography (PET), etc. The training input images for each domain can be received by loading a number of previously stored medical images from a database of medical images. In some embodiments, the output images corresponding to the training input images from a domain may be existing images that are stored in a database. In this case, the ground truth output images are received by loading the previously stored ground truth output image corresponding to each training input image. In other embodiments, ground truth output images can be generated automatically or semi-automatically from the received training input images from a domain by converting manual annotations or existing results of the target medical image analysis task to the output images defined for the target medical image analysis task.

Steps 504-512 of the method of FIG. 5 iteratively update parameters (weights) of the discriminator D 408, the decoder D 406, the first encoder $F^A$ 402 and the second encoder $F^B$ 404 to optimize a minimax objective function. The parameters (weights) of the discriminator D 408, the decoder D 406, the first encoder $F^A$ 402 and the second encoder $F^B$ 404 can be initialized using randomized weights, weights from other DI2IN and/or discriminator networks trained for other medical image analysis tasks, or any other default initial values. In an advantageous embodiment, given the M training pairs $\{(I^A_m, J^A_m)\}$ from domain A and the N training pairs $\{(I^B_n, J^B_n)\}$ from domain B, the task in training is to learn the network parameters (weights) for $F^A$ 402, $F^B$ 404, G 406, and D 408 that yield the optimal solution the following objective/cost function, in which the expectation values are replaced by sample averages:

$$\min_{F^A, F^B, G} \left\{ \frac{1}{M} \sum_m C(J^A_m, G(F^A(I^A_m))) + \frac{1}{N} \sum_n C(J^B_n, G(F^B(I^B_n))) + \max_D \left[ \frac{1}{M} \sum_m \log(D(F^A(I^A_m))) + \frac{1}{N} \sum_n \log(1 - D(F^B(I^B_m))) \right] \right\}. \quad (5)$$

In the cost function of Equation (5), the first term is a cost related to error between the ground truth output images for domain A and the predicted output images generated by the first encoder $F^A$ 402 and the decoder G 406 from the training input images from domain A. The second term is a cost related to error between the ground truth output images for domain B and the predicted output images generated by the second encoder $F^B$ 404 and the decoder G 406 from the training input images from domain B. The third term is a cost related to classification by the discriminator D 408 of the feature maps generated by the first encoder $F^A$ 402 from the training input images from domain A. The fourth term is a cost related to classification by the discriminator D 408 of the feature maps generated by the second encoder $F^B$ 404 from the training input images from domain B. The optimization of the objective function of Equation (5) is achieved by iterating steps 504-510.

At step 504, with the parameters of the first encoder $F^A$ 402 and the second encoder $F^B$ 404 fixed, the parameters of the discriminator D 408 are learned to solve the following maximization task:

$$\max_D \frac{1}{M} \sum_m \log(D(F^A(I^A_m))) + \frac{1}{N} \sum_n \log(1 - D(F^B(I^B_m))). \quad (6)$$

In this step, the parameters of the discriminator D 408 are learned by adjusting the parameters of the discriminator D 408 to maximize/increase the positive classification by the discriminator D 408 of the feature maps generated by the first encoder $F^A$ 402 from the training input images from domain A and the negative classification by the discriminator D 408 of the feature maps generated by the second encoder $F^B$ 404 from the training input images from domain B over the respective training sets for domains A and B. Since, as described above, a deep neural network is used to model the discriminator D 408, this minimization task can be performed using a backpropagation step implemented based on a minibatch of training pairs.

At step 506, with the parameters of the first encoder $F^A$ 402 and the second encoder $F^B$ 404 fixed, the parameters of the decoder G 406 are learned to solve the following minimization task:

$$\min_G \frac{1}{M} \sum_m C(J^A_m, G(F^A(I^A_m))) + \frac{1}{N} \sum_n C(J^B_n, G(F^B(I^B_n))). \quad (7)$$

In this step, the parameters of the decoder G 406 are learned by adjusting the parameters of the decoder G 406 to minimize/decrease the error between the ground truth output images for domain A and the predicted output images generated by the first encoder $F^A$ 402 and the decoder G 406 from the training input images from domain A and the error between the ground truth output images for domain B and the predicted output images generated by the second encoder $F^B$ 404 and the decoder G 406 from the training input images from domain B over the respective training sets for domains A and B. Since, the decoder G 406 is a deep neural network, this minimization task can be performed using a backpropagation step implemented based on a minibatch of training pairs. In a possible implementation, steps 504 and 506 can be performed in parallel.

At step 508, with the parameters of the decoder G 406 and the discriminator D 408 fixed, the parameters of the first encoder $F^A$ 402 are learned to solve the following minimization task:

$$\min_{F^A} \frac{1}{M} \sum_m C(J_m^A, G(F^A(I_m^A))) + \frac{1}{M} \sum_m \log(D(F^A(I_m^A))). \qquad (8)$$

In this step, the parameters of the first encoder $F^A$ 402 are learned by adjusting the parameters of the first encoder $F^A$ 402 to minimize/decrease the error between the ground truth output images for domain A and the predicted output images generated by the first encoder $F^A$ 402 and the decoder G 406 from the training input images from domain A and to minimize/decrease the positive classification by the discriminator D 408 of the feature maps generated by the first encoder $F^A$ 402 from the training input images from domain A over the training set for domain A. The second term of this minimization problem forces the first encoder $F^A$ 402 to learn parameters that will result in the distribution of the feature maps generated by the first encoder $F^A$ 402 for domain A to be closer to the distribution of the feature maps generated by the second encoder $F^B$ 404 in order to decrease the accuracy of the discriminator D 408 in positively classifying the feature maps generated by the first encoder $F^A$ 402. Thus, knowledge from domain B is integrated into the training of the first encoder $F^A$ 402 for domain A. Since, the first encoder $F^A$ 402 is a deep neural network, this minimization task can be performed using a backpropagation step implemented based on a minibatch of training pairs.

At step 510, with the parameters of the decoder G 406 and the discriminator D 408 fixed, the parameters of the second encoder $F^B$ 404 are learned to solve the following minimization task:

$$\min_{F^B} \frac{1}{N} \sum_n C(J_n^B, G(F^B(I_n^B))) + \frac{1}{N} \sum_n \log(1 - D(F^B(I_m^B))). \qquad (9)$$

It is practically found that rather than minimizing log(1−D), maximizing log(D) leads to better gradient signals early in learning, yet both objective functions yield the same fixed point. Accordingly, in an advantageous implementation, the parameters of the second encoder $F^B$ 404 can be learned in step 510 using the following minimization problem:

$$\min_{F^B} \frac{1}{N} \sum_n C(J_n^B, G(F^B(I_n^B))) - \frac{1}{N} \sum_n \log(D(F^B(I_m^B))). \qquad (10)$$

In this step, the parameters of the second encoder $F^B$ 404 are learned by adjusting the parameters of the second encoder $F^B$ 404 to minimize/decrease the error between the ground truth output images for domain B and the predicted output images generated by the second encoder $F^B$ 404 and the decoder G 406 from the training input images from domain B and to maximize/increase the positive classification (or minimize/decrease the negative classification) by the discriminator D 408 of the feature maps generated by the second encoder $F^B$ 404 from the training input images from domain B over the training set for domain B. The second term of this minimization problem forces the second encoder $F^B$ 404 to learn parameters that will result in the distribution of the feature maps generated by the second encoder $F^B$ 404 for domain B to be closer to the distribution of the feature maps generated by the first encoder $F^A$ 402 in order to decrease the accuracy of the discriminator D 408 in negatively classifying the feature maps generated by the second encoder $F^B$ 404. Thus, knowledge from domain A is integrated into the training of the second encoder $F^B$ 404 for domain B. Since, the second encoder $F^B$ 404 is a deep neural network, this minimization task can be performed using a backpropagation step implemented based on a minibatch of training pairs. In a possible implementation, steps 508 and 510 can be performed in parallel.

At step 512, it is determined whether a stop condition has been reached. If the stop condition has not yet been reached, the method returns to step 504 and performs another iteration of steps 504-510. If the stop condition has been reached, the method proceeds to step 514. In an advantageous implementation, the stop condition is convergence of the network parameters (weights) of $F^A$ 402, $F^B$ 404, G 406, and D 408. In this case, steps 504, 506, 508, and 510 are repeated until the weights of $F^A$ 402, $F^B$ 404, G 406, and D 408 converge. The stop condition could also be met when a predetermined maximum number of iterations has been reached.

At step 514, once the stop condition is reached, the training ends. The trained cross-domain DI2IN 400, including the first encoder $F^A$ 402 for domain A, the second encoder $F^B$ 404 for domain B, and the decoder G 406, is stored in a memory or storage of a computer system and then used in the inference stage to generate an output images providing results of the target medical image analysis task for newly received medical images input to the cross-domain DI2IN 400.

Returning to FIG. 3, in the inference stage, at step 302, a medical image of a patient from domain A or domain B is received. The medical image can be a 2D or 3D medical image acquired using any type of medical imaging modality, such as CT, MR, DynaCT, ultrasound, PET, etc. The medical image may be received directly from an image acquisition device used to acquire the input medical image, such as a CT scanner, MR scanner, etc. Alternatively, the medical image may be received by loading a previously acquired medical image from a storage or memory of a computer system or receiving a medical image that has been transmitted from a remote computer system.

At step 304, it is determined whether the received medical image is from domain A or domain B. If the received medical image is from domain A, the method proceeds to step 306. If the received medical image is from domain B, the method proceeds to step 308.

At step 306, if the received medical image from domain A, the received medical image is input to the first encoder $F^A$ 402 of the trained cross-domain DI2IN 400 and the first encoder $F^A$ 402 converts the received medical image to a feature map $F^A(I^A)$. The method then proceeds to step 310.

At step 308, if the received medical image from domain B, the received medical image is input to the second encoder $F^B$ 404 of the trained cross-domain DI2IN 400 and the second encoder $F^B$ 404 converts the received medical image to a feature map $F^B(I^B)$. The method then proceeds to step 310.

At step 310, the decoder G 406 generates an output image providing the result of the target medical image analysis task for the received medical image from the feature map generated (at step 306 or step 308) for the received medical image. The decoder G 406 is trained to generate output images from feature maps generated by the first encoder $F^A$ 402 (from medical images from domain A) and feature maps generated by the second encoder $F^B$ 404 (from medical images from domain B). Accordingly, if the received medical image is from domain A, the output image is generated as $J^A = G(F^A(I^A))$ by invoking the encoding network (encoder) $F^A$ 402 for domain A followed by the shared decoding network (decoder) G 406. If the received medical image is from domain B, the output image is generated as $J^B=G(F^B(I^B))$ by invoking the encoding network (encoder) $F^B$ 404 for domain B followed by the shared decoding network (decoder) G 406.

At step 312, the generated output image, which provides the result of the target medical image analysis task for the received medical image, is output. For example, the generated output image can be output by displaying the generated output image on a display device of a computer system. The generated output image can also be output by storing the generated output image on a memory or storage of a computer system or by transmitting the generated output image to a remote computer system.

Cross-domain medical image synthesis is an important medical image analysis task with numerous applications. For example, for a medical imaging modality with insufficient training data for training machine learning algorithms, synthesized images can be used as augmented training images. For multi-model image registration, a synthesized image of one modality generated from an image of another modality can serve as a bridge between the two modalities and may be used to define a similarity metric for the multi-model image registration. In addition, cross-domain medical image synthesis may be used to render, from a medical image acquired from a low-end image acquisition device, a synthesized image that appears as if it were acquired from a high-end image acquisition device.

Embodiments of the present invention provide methods for deep learning based cross-domain synthesis of medical images. Embodiments of the present invention train deep neural networks for cross-domain medical image synthesis that can be used to synthesize medical images in a target domain from available images in a source domain without having to perform image acquisition in the target domain. Embodiments of the present invention may be used to synthesize target domain medical images in order to create large training set of target domain medical images for training machine learning based classifiers for anatomical object detection, segmentation, tracking, and classification, without having to perform additional image acquisition on a large number of subjects. In addition, embodiments of the present invention may be used to synthesize target domain medical images for other applications, such as to create visualization tools for virtual domains, to perform cross-modality registration, to up-sample the resolution of image data, or for image segmentation. As used herein, cross-domain synthesis refers to synthesis of medical images across medical imaging modalities, such as synthesizing a CT image from an MR image, as well as synthesis of images across an image domain, such MR images with different protocols (e.g., T1 and T2), contrast CT images and non-contrast CT images, CT image captured with low kV and CT images captured with high kV, or any type of low resolution medical image to a corresponding high resolution medical image. That is, the "source domain" and "target domain" may be completely different medical imaging modalities or different image domains or protocols within the same overall imaging modality.

Suppose that given an input image I of size m x n, we aim to synthesize an output image J of the same size. Note that we use 2D as a working example, but it is straightforward extend this to 3D or even higher dimensions. In a traditional patch-based method, for each pixel x with an intensity I(x) in the input image I, an image patch $I_p[x]$ centered around the pixel is cropped and a nonlinear mapping function $J(x)=f(I_p[x])$ is learned that outputs the intensity J(x) in the output image J. Many machine learning methods can be used, including k-nearest neighbor, support vector regression, random regression forest, boosting regression, etc. Recently, neural networks, such as a convolutional neural network (CNN), have been used for learning such a mapping function for patch-based image synthesis. The benefits of using a CNN lie in its powerful hierarchical feature representation and efficient computation.

A deep DI2IN is a universal variant of CNN that has applications for medical image analysis tasks beyond image synthesis, including landmark detection, image segmentation, image registration etc. In a possible implementation, a deep image-to-image network (DI2IN), such as the DI2IN 100 of FIG. 1 described above, can be used for cross-domain medical image synthesis. In this case, the input image I is a medical image from a source domain and the output image J is medical image in a target domain.

Figure 6:
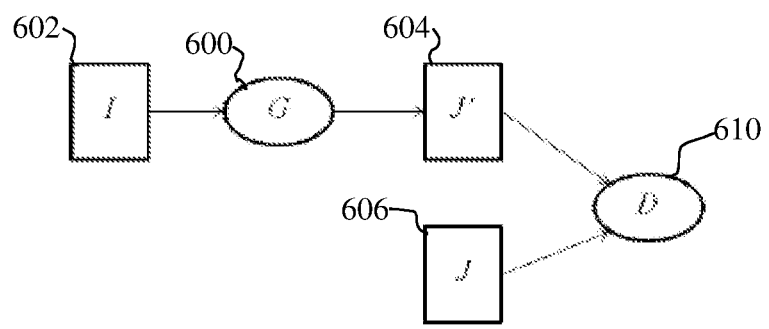
FIG. 6 illustrates a generative adversarial network (GAN) for cross-domain medical image synthesis according to an embodiment of the present invention.

A generative adversarial network (GAN) is described above and illustrated in FIG. 2. The GAN can be extended to cross-domain medical image synthesis in which a synthesized medical image J in a target domain B is generated from an input medical image I is a source domain A. FIG. 6 illustrates a generative adversarial network (GAN) for cross-domain medical image synthesis according to an embodiment of the present invention. As shown in FIG. 6, the GAN includes a generator network G 600 and a discriminator network 610. An input image I 602 in a source domain is input to the generator G 600. The generator G 600 is a deep neural network that generates a synthesized output image J' 604 in a target domain from the input image I 602. In an exemplary implementation, the generator G can be implemented using a DI2IN, such as the DI2IN 100 of FIG. 1. The synthesized output image J' 604 and a real image J 606 in the target domain are input to a discriminator D 610. The discriminator D 610 is another deep neural network that distinguishes between the synthesized output imager J' 604 and the real image J 606 in the target domain. In particular, the discriminator D 610 classifies each image as real (positive) or synthesized (negative). During training, the generator G 600 and the discriminator D 610 together play the following minimax game:

$$\min_G \max_D E_{J \sim p(J)}[\log(D(J))] + E_{I \sim p(I)}[\log(1-D(J'=G(I)))]. \quad (11)$$

The networks are trained end-to-end by iteratively adjusting the parameters (weights) of the discriminator D 610 and the generator G 600 to optimize the minimax objective function in Equation (1). In Equation (1), the first term is a cost related to classification of the real sample J 606 by the discriminator D 610 and the second term is a cost related to the synthesized sample J' 604 by the discriminator D 610. The discriminator D 610 maximizes the function (i.e., trying its best to distinguish between the real and synthesized samples) and the generator G 600 minimizes the function (i.e., synthesize real looking samples to fool the discriminator). The generator G 600 and the discriminator D 610 evolve dynamically in the sense of learning better network parameters until they reach equilibrium, that is, the synthesized sample J' 604 becomes indistinguishable (or as close as possible from being indistinguishable) from the real sample J 606 through the eyes of the discriminator D 610. Note that the medical image synthesis using the GAN of FIG. 6 is unilateral in that it is from a source domain A to a target domain B. In order to reverse the source and target domain and perform medical image synthesis from domain B to domain A, and independent synthesis pipeline is needed.

Figure 7:
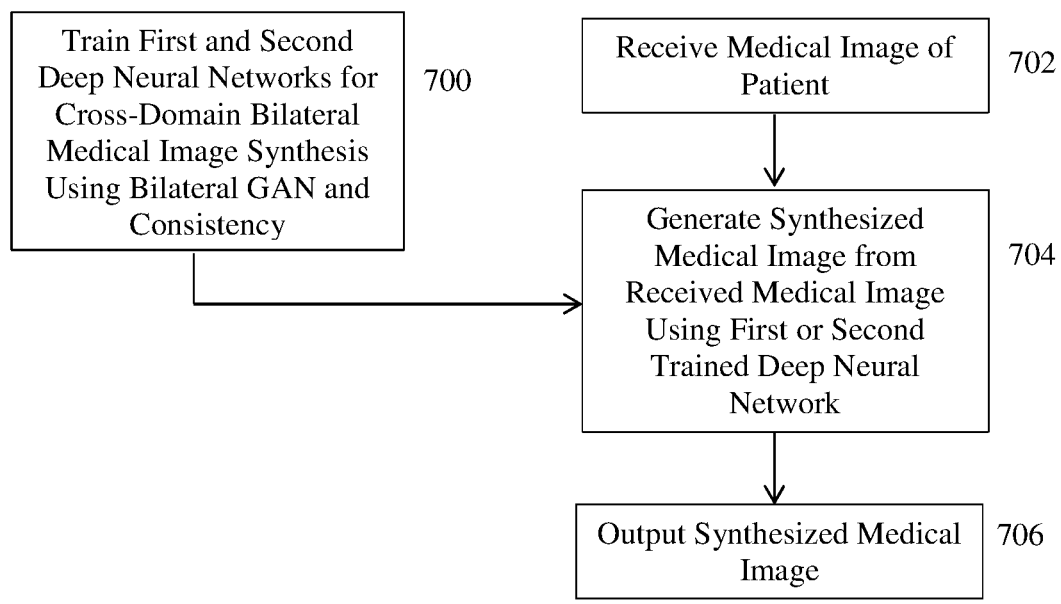
FIG. 7 illustrates a method for cross-domain bilateral medical image synthesis according to an embodiment of the present invention.

FIG. 7 illustrates a method for cross-domain bilateral medical image synthesis according to an embodiment of the present invention. The method of FIG. 7 includes a training stage (step 700) and an inference stage (steps 702-706). The training stage (step 700) is performed to train first and second deep neural networks together for cross-domain bilateral medical image synthesis. The inference stage (steps 702-706) performs medical image synthesis using at least one of the trained deep neural networks resulting from the training stage. Once the first and second deep neural networks for cross-domain bilateral medical image synthesis are trained in the training stage, the inference stage can be repeated for newly received medical images to generate synthesized medical images in a second domain from received medical images in a first domain and to generate synthesized medical images in the first domain from received medical images in the second domain.

Figure 8:
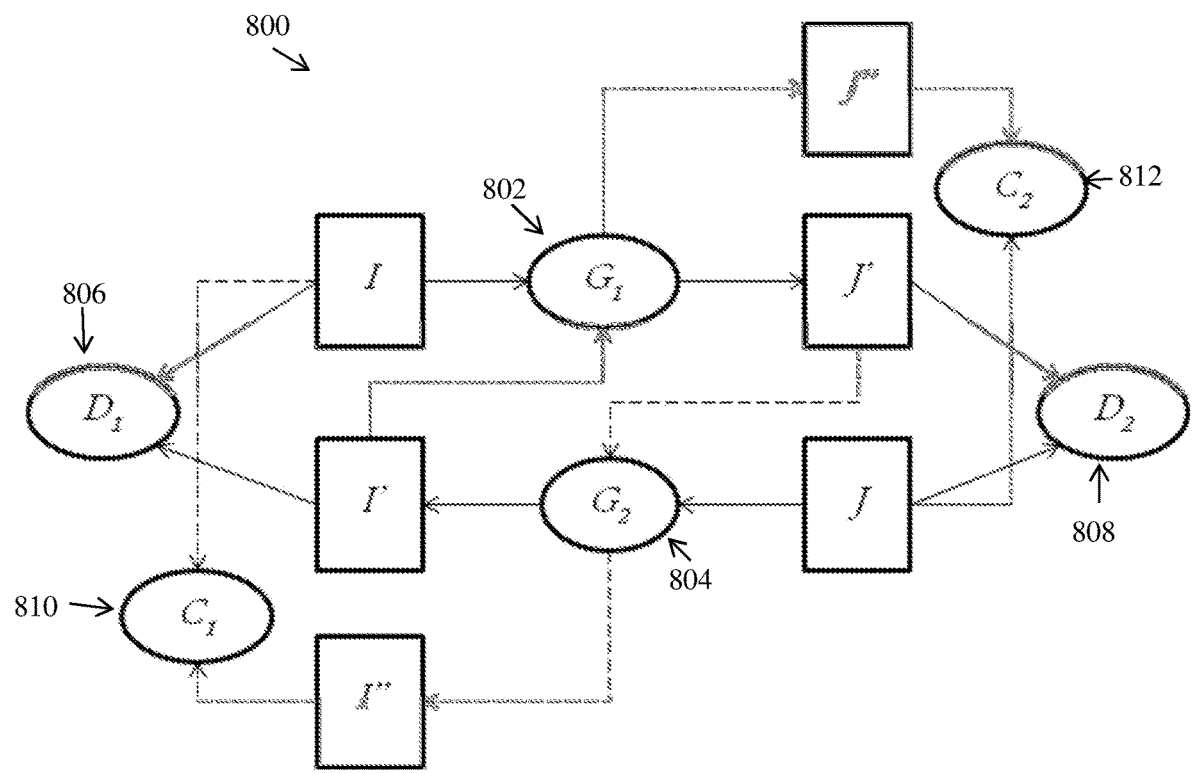
FIG. 8 illustrates a bilateral GAN for training deep neural networks for cross-domain medical image synthesis according to an embodiment of the present invention.

At step 700, in the training stage, first and second deep neural networks for bilateral medical image synthesis are trained using a bilateral GAN and consistency. FIG. 8 illustrates a bilateral GAN 800 for training deep neural networks for cross-domain medical image synthesis according to an embodiment of the present invention. As shown in FIG. 8, the bilateral GAN 800 includes a first generator network $G_1$ 802 for generating synthesized images of a second domain (e.g., domain B) from input images of a first domain (e.g., domain A) and a second generator network $G_2$ 804 for generating synthesized images of the first domain from input images of the second domain. $G_1$ 802 and $G_2$ 804 are first and second deep neural networks for medical image synthesis. For example, $G_1$ 802 and $G_2$ 804 can be implemented using respective DI2INs. $G_1$ 802 performs medical image synthesis from domain A to domain B, and $G_2$ 804 performs medical image synthesis from domain B to domain A. $G_1$ 802 and $G_2$ 804 are trained together in the bilateral GAN 800, resulting in first and second deep neural networks for bilateral medical image synthesis. The bilateral GAN 800 also includes a first discriminator network $D_1$ 806 for distinguishing between real training images in the first domain and synthesized images in the first domain generated by the second generator $G_2$ 804 from input training images in the second domain, and a second discriminator network $D_2$ 808 for distinguishing between real images in the second domain and synthesized images in the second domain generated by the first generator $G_1$ 802 from input training images in the first domain.

The first generator $G_1$ 802 generates a synthesized image I' of the second domain from an input training image I of the first domain. The second generator $G_2$ 804 generates a synthesized image I' of the first domain from an input training image J of the second domain. The first generator $G_1$ 802 also generates a synthesized image J" of the second domain from the synthesized image I' of the first domain generated by the second generator $G_2$ 804 from the input training image J of the second domain. The second generator $G_2$ 804 also generates a synthesized image I" of the first domain from the synthesized image J' of the second domain generated by the first generator $G_1$ 806 from the input training image I of the first domain. The first discriminator $D_1$ 806 inputs the real training images I of the first domain and the synthesized images I' of the first domain generated by $G_2$ 804 from the training images J of the second domain and classifies the real training images I and the synthesized images I' as real (positive) or synthesized (negative) by computing a probability/classification score for each image. The second discriminator $D_2$ 808 inputs the real training images J of the second domain and the synthesized images J' of the second domain generated by $G_1$ 802 from the training images I of the first domain and classifies the real training images J and the synthesized images J' as real (positive) or synthesized (negative) by computing a probability/classification score for each image.

According to an advantageous embodiment, the bilateral GAN 800 of FIG. 8 trains the image synthesis pipelines in both directions together by adding constraints to the training that try to make sure the following consistency holds: $I=I''=G_2(J')=G_2(G_1(I))$ and $J=J''=G_1(I')=G_1(G_2(J))$. That is, the image I" synthesized from the image J' synthesized from image I should be consistent with the original image I, and the image J" synthesized from the imge I' synthesized from image J should be consistent with the original image J. As shown in FIG. 8, a first cost function $C_1$ 810 compares the training images I in the first domain and the synthesized images I" in the first domain, and a second cost function $C_2$ 812 compares the training images J in the second domain and the synthesized images J" in the second domain. In an advantageous implementation, the first cost function $C_1$ 810 computes a pixel-wise (or voxel-wise) error between the each training image I in the first domain and the respective synthesized image I" synthesized from the synthesized image J' synthesized from that training image I. Since the synthesized image I" can be traced back the original image I, they can be directly compared using a pixel-wise cost function to measure the consistency between the images. In an advantageous implementation, the second cost function $C_2$ 812 computes a pixel-wise (or voxel-wise) error between the each training image J in the second domain and the respective synthesized image J" synthesized from the synthesized image I' synthesized from that training image J. Since the synthesized image J" can be traced back the original image J, they can be directly compared using a pixel-wise cost function to measure the consistency between the images.

The training of the bilateral GAN 800 of FIG. 8 aims to optimize the following objective function, which includes two minimax games:

$$\min_{G_1} \min_{G_2} \begin{cases} \max_{D_1} [E_{I \sim p(I)} \log(D_1(I)) + E_{J \sim p(J)} \log(1 - D_1(G_2(J)))] + \\ E_{I \sim p(I)} C_1(I, G_2(G_1(I))) + \\ \max_{D_2} [E_{J \sim p(J)} \log(D_2(J)) + E_{I \sim p(I)} \log(1 - D_2(G_1(I)))] + \\ E_{J \sim p(J)} C_2(J, G_1(G_2(J))) \end{cases} \quad (12)$$

The terms related to the cost functions $C_1$ 810 and $C_2$ 812 reward consistency between I and I" and between J and J" during training. The use of the bilateral GAN 800 of FIG. 8 with the consistency constraints allows the training to be performed with independent sets of training images in the first and second domains. That is, paired training data from the same patient in both domains is not required for training the deep learning networks for cross-domain bilateral image synthesis.

Figure 9:
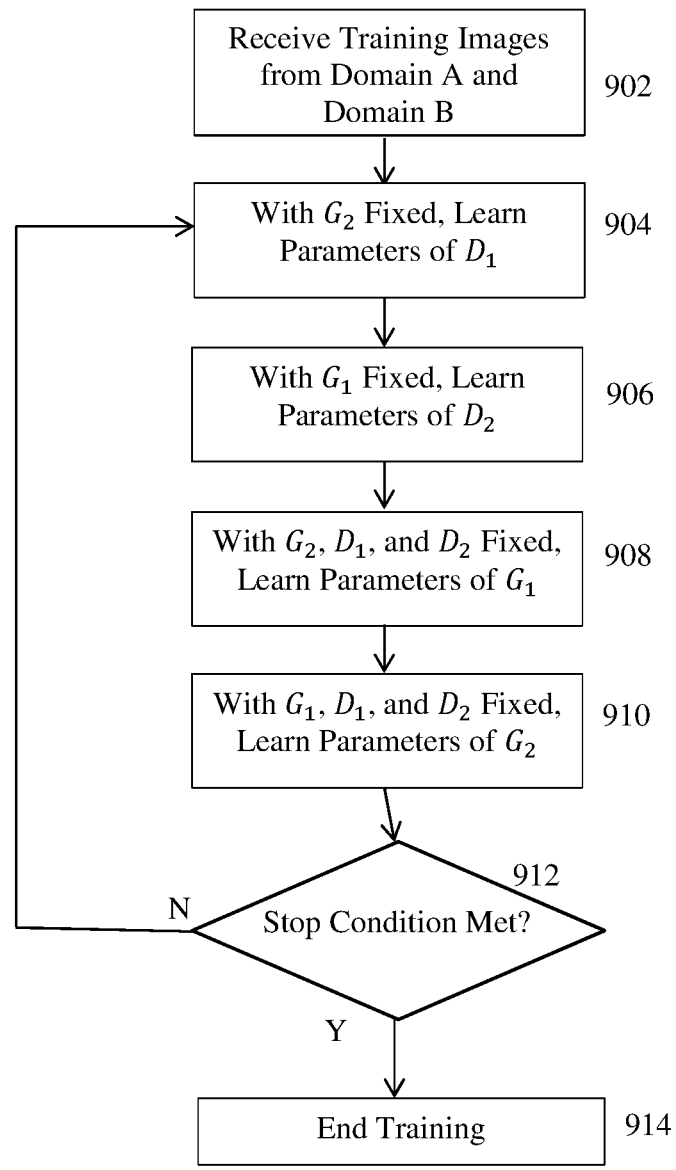
FIG. 9 illustrates a method for training deep neural networks for cross-domain bilateral medical image synthesis according to an embodiment of the present invention.

FIG. 9 illustrates a method for training deep neural networks for cross-domain bilateral medical image synthesis according to an embodiment of the present invention. The method of FIG. 9 can be used to train the bilateral GAN 800 of FIG. 8 in order to implement step 700 of FIG. 7. At step 902, training images from the first domain A and the second domain B are received. In particular, a first set of M training images $\{I_m; m=1: M\}$ from domain A and a second set of N training images $\{J_n; n=1: N\}$ from domain B. The first set of training images $I_m$ of domain A and the second set of training images $J_n$ of domain B can be independent sets of image and do not need to have corresponding training images in domains A and B from the same patients. The training images from each domain are medical images acquired using a medical imaging modality corresponding to the domain, such as computed tomography (CT), magnetic resonance (MR), DynaCT, ultrasound, x-ray, positron emission tomography (PET), etc. The training images for each domain can be received by loading a number of previously stored medical images from a database of medical images.

Steps 904-912 of the method of FIG. 9 iteratively update parameters (weights) of the first generator $G_1$ 802, the second generator $G_2$ 804, the first discriminator $D_1$ 806, and the second discriminator $D_2$ 808 to optimize a minimax objective function. The parameters (weights) of the first generator $G_1$ 802, the second generator $G_2$ 804, the first discriminator $D_1$ 806, and the second discriminator $D_2$ 808 can be initialized using randomized weights, weights from other DI2IN and/or discriminator networks trained for other medic image synthesis tasks or other medical image analysis tasks, or any other default initial values. In an advantageous embodiment, given the M training images $\{I_m; m=1: M\}$ from domain A and the N training images $\{J_n; n=1: N\}$ from domain B, the task in training is to learn the network parameters (weights) for the first generator $G_1$ 802, the second generator $G_2$ 804, the first discriminator $D_1$ 806, and the second discriminator $D_2$ 808 that yield the optimal solution the following objective function, in which the expectation values are replaced by sample averages:

$$\min_{G_1} \min_{G_2} \begin{cases} \max_{D_1} \left[ \frac{1}{M} \sum_m \log(D_1(I_m)) + \frac{1}{N} \sum_n \log(1 - \\ D_1(G_2(J_n))] + \frac{1}{M} \sum_m C_1(I_m, G_2(G_1(I_m))) + \\ \max_{D_2} \left[ \frac{1}{N} \sum_n \log(D_2(J_n)) + \frac{1}{M} \sum_m \log(1 - \\ D_2(G_1(I_m))] + \frac{1}{N} \sum_n C_2(J_n, G_1(G_2(J_n))) \end{cases} \quad (13)$$

The optimization of the objective function of Equation (13) is achieved by iterating steps 904-910.

At step 904, with the parameters of the second generator $G_2$ 804 fixed, the parameters of the first discriminator $D_1$ 806 are learned to solve the following maximization task:

$$\max_{D_1} \left[ \frac{1}{M} \sum_m \log(D_1(I_m)) + \frac{1}{N} \sum_n \log(1 - D_1(G_2(J_n))) \right]. \quad (14)$$

In this step, the parameters of first discriminator $D_1$ 806 are learned by adjusting the parameters of the first discriminator $D_1$ 806 to maximize/increase the positive classification by the first discriminator $D_1$ 806 of the real training images $I_m$ of domain A and the negative classification by the first discriminator $D_1$ 806 of the synthesized images $I'=G_2(J_n)$ generated by the second generator $G_2$ 804 from the training images $J_n$ of domain B over the respective training sets for domains A and B. Since a deep neural network is used to model the first discriminator $D_1$ 806, this maximization task can be performed using a backpropagation step implemented based on two mini-batches of training images, one from domain A and the other from domain B.

At step 906, with the parameters of the first generator $G_1$ 802 fixed, the parameters of the second discriminator $D_2$ 808 are learned to solve the following maximization task:

$$\max_{D_2} \left[ \frac{1}{N} \sum_n \log(D_2(J_n)) + \frac{1}{M} \sum_m \log(1 - D_2(G_1(I_m))) \right]. \quad (15)$$

In this step, the parameters of second discriminator $D_2$ 808 are learned by adjusting the parameters of the second discriminator $D_2$ 808 to maximize/increase the positive classification by the second discriminator $D_2$ 808 of the real training images $J_n$ of domain B and the negative classification by the second discriminator $D_2$ 808 of the synthesized images $J'=G_1(I_m)$ generated by the first generator $G_1$ 802 from the training images $I_m$ of domain A over the respective training sets for domains B and A. Since a deep neural network is used to model the second discriminator $D_2$ 808, this maximization task can be performed using a backpropagation step implemented based on two mini-batches of training images, one from domain A and the other from domain B. In a possible implementation, steps 904 and 906 can be performed in parallel.

At step 908, with the parameters of the second generator $G_2$ 804, the first discriminator $D_1$ 806, and the second discriminator $D_2$ 808 fixed, the parameters of the first generator $G_1$ 802 are learned to solve the following minimization task:

$$\min_{G_1} \frac{1}{M} \sum_m C_1(I_m, G_2(G_1(I_m))) + \quad (16)$$

$$\frac{1}{N} \sum_n C_2(J_n, G_1(G_2(J_n))) + \frac{1}{M} \sum_m \log(1 - D_2(G_1(I_m))).$$

In this step, the parameters of the first generator $G_1$ 802 are learned by adjusting the parameters of the first generator $G_1$ 802 to minimize/decrease the error between the training images $I_m$ of domain A and the synthesized output images $I''=G_2(G_1(I_m))$ generated by the second generator $G_2$ 804 from the synthesized images $J'$ of domain B generated by the first generator $G_1$ 802 from the training images $I_m$ of domain A over the training set of domain A, to minimize/decrease the error between the training images $J_n$ of domain B and the synthesized output images $J''=G_1(G_2(J_n))$ generated by the first generator $G_1$ 802 from the synthesized images $I'$ of domain A generated by the second generator $G_2$ 804 from the training images $J_n$ of domain B over the training set of domain B, and to minimize/decrease the negative classification (or to maximized/increase the positive classification) by the second discriminator $D_2$ 808 of the synthesized images $J'=G_1(I_m)$ generated by the first generator $G_1$ 802 from the training images $I_m$ of domain A over the training set of domain A. Since the first generator $G_1$ 802 is a deep neural network, this minimization task can be performed using a backpropagation step implemented based on two mini-batches of training images, one from domain A and the other from domain B.

At step 910, with the parameters of the first generator $G_1$ 802, the first discriminator $D_1$ 806, and the second discriminator $D_2$ 808 fixed, the parameters of the second generator $G_2$ 804 are learned to solve the following minimization task:

$$\min_{G_2} \frac{1}{M} \sum_m C_1(I_m, G_2(G_1(I_m))) + \quad (17)$$

-continued $$\frac{1}{N}\sum_{n} C_2(J_n, G_1(G_2(J_n))) + \frac{1}{N}\sum_{n} \log(1 - D_1(G_2(J_n))).$$

In this step, the parameters of the second generator $G_2$ 804 are learned by adjusting the parameters of the second generator $G_2$ 804 to minimize/decrease the error between the training images $I_m$ of domain A and the synthesized output images $I''=G_2(G_1(I_m))$ generated by the second generator $G_2$ 804 from the synthesized images J' of domain B generated by the first generator $G_1$ 802 from the training images $I_m$ of domain A over the training set of domain A, to minimize/decrease the error between the training images $J_n$ of domain B and the synthesized output images $J''=G_1(G_2(J_n))$ generated by the first generator $G_1$ 802 from the synthesized images I' of domain A generated by the second generator $G_2$ 804 from the training images $J_n$ of domain B over the training set of domain B, and to minimize/decrease the negative classification (or to maximized/increase the positive classification) by the first discriminator $D_1$ 806 of the synthesized images $I'=G_2(J_n)$ generated by the second generator $G_2$ 804 from the training images $J_n$ of domain B over the training set of domain B. Since the second generator $G_2$ 804 is a deep neural network, this minimization task can be performed using a backpropagation step implemented based on two mini-batches of training images, one from domain A and the other from domain B.

In steps 908 and 910, it is practically found that rather than minimizing $\log(1-D)$, maximizing $\log(D)$ (minimizing $-\log(D)$) leads to better gradient signals early in learning, yet both objective functions yield the same fixed point.

At step 912, it is determined whether a stop condition has been reached. If the stop condition has not yet been reached, the method returns to step 904 and performs another iteration of steps 904-910. If the stop condition has been reached, the method proceeds to step 914. In an advantageous implementation, the stop condition is convergence of the network parameters (weights) of the first generator $G_1$ 802, the second generator $G_2$ 804, the first discriminator $D_1$ 806, and the second discriminator $D_2$ 808. In this case, steps 904, 906, 908, and 910 are repeated until the weights of the first generator $G_1$ 802, the second generator $G_2$ 804, the first discriminator $D_1$ 806, and the second discriminator $D_2$ 808 converge. The stop condition could also be met when a predetermined maximum number of iterations has been reached.

At step 914, once the stop condition is reached, the training ends. The trained first generator $G_1$ 802 and the trained second generator $G_2$ 804 are stored in a memory or storage of a computer system and then used in the inference stage to perform cross-domain bilateral medical image synthesis. In particular, the trained first generator $G_1$ 802 is used to generate a synthesized medical image of domain B from an input medical image of domain A, and the trained second generator $G_2$ is used to generate a synthesized medical image of domain A from an input medical image of domain B.

Returning to FIG. 7, in the inference stage, at step 702, a medical image of a patient from domain A or domain B is received. The medical image can be a 2D or 3D medical image acquired using any type of medical imaging modality, such as CT, MR, DynaCT, ultrasound, PET, etc. The medical image may be received directly from an image acquisition device used to acquire the input medical image, such as a CT scanner, MR scanner, etc. Alternatively, the medical image may be received by loading a previously acquired medical image from a storage or memory of a computer system or receiving a medical image that has been transmitted from a remote computer system.

At step 704, a synthesized medical image is generated from the received medical image using the first or second trained deep neural network. The first and second trained deep neural networks are the trained first generator $G_1$ 802 and the trained second generator $G_2$ 804, respectively. If the received medical image is from the domain A, the trained first generator $G_1$ 802 is used to generate a synthesized medical image of domain B from the received medical image. If the received medical image is from the domain B, the trained second generator $G_2$ 804 is used to generate a synthesized medical image of domain A from the received medical image.

At step 706, the synthesized medical image is output. For example, the synthesized medical image can be output by displaying the synthesized medical image on a display device of a computer system. The synthesized medical image can also be output by storing the synthesized medical image on a memory or storage of a computer system or by transmitting the synthesized medical image to a remote computer system.

As illustrated in FIG. 6 and described above, the GAN framework can be extended to cross-domain medical image synthesis. However, the GAN framework may be limited by discrepancies between the available training datasets in the two domains. To understand such limitations, CT-to-MR image synthesis can be used as an example. The number CT images available is often much larger than the number of available MR images. Further, the patients from which the CT scans were acquired may be in a different population subgroup than the patients from which the MR scans were acquired. This may result in a statistically significant shift in the training images from the two domains, and may cause the discriminator in the GAN framework to distinguish between the two domains based on differences between properties, such as anatomical properties, in the population subgroups from which the training samples for the different domains were acquired.

In an advantageous embodiment of the present invention, the shift between the training samples in the two domains is addressed in training the GAN framework. In this embodiment of the present invention, a shift in the anatomical geometry between the training samples in the two domains is compensated for in the training of the GAN. It is to be understood that the training framework described herein can also be extended to handle shifts in other properties as well.

Figure 10:
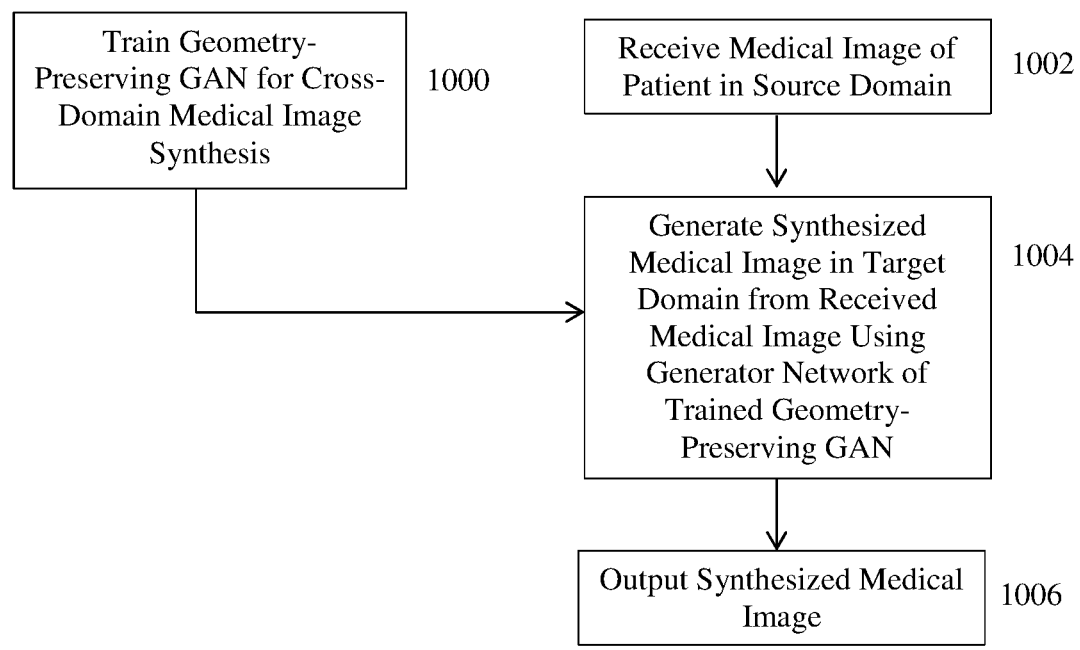
FIG. 10 illustrates a method for cross-domain medical image synthesis using a geometry preserving generative adversarial network according to an embodiment of the present invention.

FIG. 10 illustrates a method for cross-domain medical image synthesis using a geometry preserving generative adversarial network according to an embodiment of the present invention. The method of FIG. 10 includes a training stage (step 1000) and an inference stage (steps 1002-1006). The training stage (step 1000) is performed to train a geometry-preserving GAN. The inference stage (steps 1002-1006) performs medical image synthesis using the generator network of the trained geometry-preserving GAN to generate a synthesized medical image in a target domain from an input medical image in a source domain. Once the geometry-preserving GAN is trained in the training stage, the inference stage can be repeated for newly received medical images to generate a synthesized medical image in the target domain from each received medical image in the source domain.

At step 1000, in the training stage, a geometry-preserving GAN is trained for cross-domain medical image synthesis. The GAN includes a generator that is a deep neural network for generating a synthesized medical image is a target domain from an input medical image in a source domain, and a discriminator that is another deep neural network for distinguishing between synthesized medical images in the target domain generated by the generator and real medical images in the target domain. The GAN framework for cross-domain medical image synthesis is illustrated in FIG. 6. In an advantageous implementation, the generator of the geometry-preserving GAN can be implemented using a deep image-to-image network (DI2IN), such as the DI2IN illustrated in FIG. 1.

Let us assume that there is a distributional shift in a certain factor 0, that is, the distributions $p_S(\theta)$ and $p_T(\theta)$ in the source and target training examples are different, i.e., the training examples in the source and target training domains exhibit different properties. In this case, the minimax objective function for the GAN can be expressed as:

$$\min_G \max_D E_{J \sim p(J), \theta \sim p_T(\theta)}[\log(D(J, \theta))] + E_{I \sim p(I), \theta \sim p_S(\theta)} [\log (1 - D(J' = G(I, \theta)))]. \quad (18)$$

Given two independent sets of training examples $\{(I_m, \theta_m)\}$ for the source domain and $\{(J_n, J_n)\}$ for the target domain, the expectation values in Equation (18) can be replaced by sample averages during training, and the minimax objective function can be expressed as:

$$\min_G \max_D \left[ \frac{1}{N} \sum_n \log(D(J_n, \theta_n)) + \frac{1}{M} \sum_m \log(1 - D(G(I_m, \theta_m))) \right]. \quad (19)$$

In an advantageous embodiment, a conditional-GAN framework is introduced to compensate for a shift in anatomical geometry between the source and target training examples:

$$\min_G \max_D \left[ \frac{1}{M} \sum_m \log(1 - D(G(I_m \mid \theta_m))) + \frac{1}{N} \sum_n \log(D(J_n, \theta_n \mid \theta_m)) \right]. \quad (20)$$

Note that in the second term in Equation (20), which is an error term based on the classification by the discriminator of the training examples of the target domain, also depends on the sample geometry $\theta_m$ in source domain. The sample geometry $\theta_m$ is the geometry of a target anatomical structure in the source domain training image $I_m$, and the sample geometry $\theta_n$ is the geometry of the target anatomical structure in the target domain training image $I_n$. In order to evaluate the value of $D(J_n, \theta_n \mid \theta_m)$, a geometric transformation $\pi$ is computed using between $\theta_m$ and $\theta_n$ (e.g., using a thin plate spline (TPS) model), and the transformation $\pi$ is used to generate a transformed target domain image $J_n^{\pi, m}$. The discriminator is than evaluated using the transformed target domain $J_n^{\pi,m}$, such that $D(J_n, \theta_n \mid \theta_m) = D(J_n^{\pi,m} \mid \theta_m)$. This rigorously preserves anatomical geometry during training. During training, the network parameters for the generator and the discriminator are learned to optimize the minimax objective function:

$$\min_G \max_D \left[ \frac{1}{M} \sum_m \log(1 - D(G(I_m \mid \theta_m))) + \frac{1}{N} \sum_n \log(D(J_n^{\pi,m} \mid \theta_m)) \right]. \quad (21)$$

The training of the generator and the discriminator of the geometry-preserving GAN is achieved by iterating the following two alternating steps:

Step 1—With the parameters of the generator G fixed, learn parameters of the discriminator D are learned to solve the following maximization task:

$$\max_D \left[ \frac{1}{M} \sum_m \log(1 - D(G(I_m \mid \theta_m))) + \frac{1}{N} \sum_n \log(D(J_n^{\pi,m} \mid \theta_m)) \right]. \quad (22)$$

Since a deep neural network is used to model the discriminator D, this maximization task can be performed using a backpropagation step implemented based on two mini-batches of training images, one from the source domain and the other from the target domain.

Step 2—With the parameters of the discriminator D fixed, learn parameters of the generator G to solve the following minimization task:

$$\min_G \left[ \frac{1}{M} \sum_m \log(1 - D(G(I_m \mid \theta_m))) \right]. \quad (23)$$

It is practically found that, rather than minimizing log(1−D), maximizing log(D) (minimizing −log(D)) leads to better gradient signals early in training, yet both objective functions yield the same fixed point. Since a deep neural network, such as a DI2IN, is used to model the discriminator G, this maximization task can be performed using a backpropagation step implemented based on two mini-batches of training images, one from the source domain and the other from the target domain Returning to FIG. 10, in the inference stage, at step 1002, a medical image of a patient in the source domain is received. The medical image can be a 2D or 3D medical image acquired using any type of medical imaging modality, such as CT, MR, DynaCT, ultrasound, PET, etc. The medical image may be received directly from an image acquisition device used to acquire the input medical image, such as a CT scanner, MR scanner, etc. Alternatively, the medical image may be received by loading a previously acquired medical image from a storage or memory of a computer system or receiving a medical image that has been transmitted from a remote computer system.

At step 1004, a synthesized medical image in the target domain is generated from the received medical image using the generator network G of the trained geometry-preserving GAN.

At step 1006, the synthesized medical image in the target domain is output. For example, the synthesized medical image can be output by displaying the synthesized medical image on a display device of a computer system. The synthesized medical image can also be output by storing the synthesized medical image on a memory or storage of a computer system or by transmitting the synthesized medical image to a remote computer system.

Figure 11:
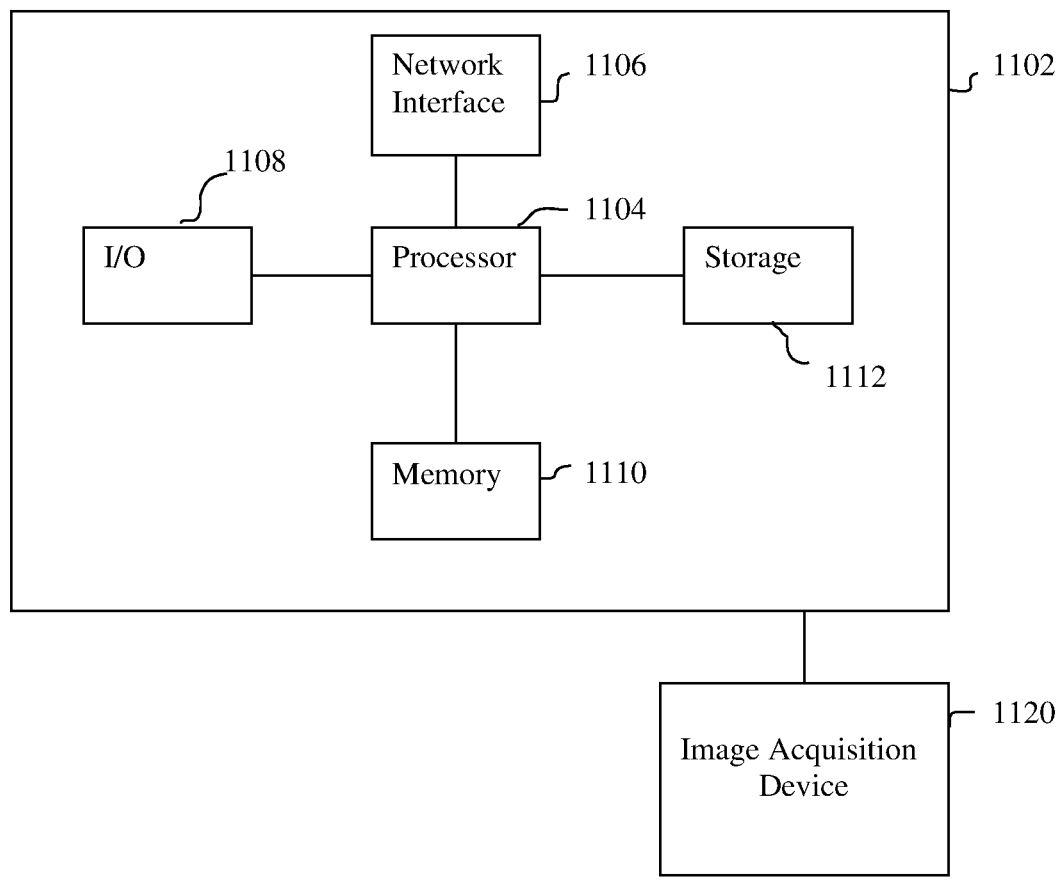
FIG. 11 is a high-level block diagram of a computer capable of implementing the present invention.

The above-described methods for cross-domain medical image analysis, cross-domain medical image synthesis, training deep neural networks for cross-domain medical image analysis, and training deep neural networks for cross-domain medical image synthesis may be implemented on a computer using well-known computer processors, memory units, storage devices, computer software, and other components. A high-level block diagram of such a computer is illustrated in FIG. 11. Computer 1102 contains a processor 1104, which controls the overall operation of the computer 1102 by executing computer program instructions which define such operation. The computer program instructions may be stored in a storage device 1112 (e.g., magnetic disk) and loaded into memory 1110 when execution of the computer program instructions is desired. Thus, the steps of the methods of FIGS. 3, 5, 7, 9, and 10 may be defined by the computer program instructions stored in the memory 1110 and/or storage 1112 and controlled by the processor 1104 executing the computer program instructions. An image acquisition device 1120, such as an MRI scanner, can be connected to the computer 1102 to input image data to the computer 1102. It is possible to implement the image acquisition device 1120 and the computer 1102 as one device. It is also possible that the image acquisition device 1120 and the computer 1102 communicate wirelessly through a network. In a possible embodiment, the computer 1102 can be located remotely with respect to the image acquisition device 1120 and the method steps described herein can be performed as part of a server or cloud based service. In this case, the method steps may be performed on a single computer or distributed between multiple networked computers. The computer 1102 also includes one or more network interfaces 1106 for communicating with other devices via a network. The computer 1102 also includes other input/output devices 808 that enable user interaction with the computer 1102 (e.g., display, keyboard, mouse, speakers, buttons, etc.). Such input/output devices 1108 may be used in conjunction with a set of computer programs as an annotation tool to annotate images/volumes received from the image acquisition device 1120. One skilled in the art will recognize that an implementation of an actual computer could contain other components as well, and that FIG. 11 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for automatically performing cross-domain based medical image analysis on a medical image of a patient, comprising:
 receiving a medical image of a patient from a first domain;
 inputting the medical image of the patient to a first encoder of a cross-domain deep image-to-image network including the first encoder for the first domain, a second encoder for a second domain, and a decoder; and
 automatically generating an output image that provides a result of a target medical image analysis task on the input medical image using the cross-domain deep image-to-image network, by the first encoder converting the input medical image from the first domain to a feature map and the decoder generating the output image from the feature map generated by the first encoder, wherein the first encoder for the first domain is trained together with the second encoder for the second domain at least in part based on a similarity of feature maps generated by the first encoder from training input images from the first domain and feature maps generated by the second encoder from training input images from the second domain, and the decoder is trained to generate output images from the feature maps generated by the first encoder and the feature maps generated by the second encoder.

2. The method of claim 1, wherein the first encoder for the first domain, the second encoder for the second domain, and the decoder of the cross-domain deep image-to-image network are trained together in an adversarial network with a discriminator network for distinguishing between the feature maps generated by the first encoder from the training input images from the first domain and the feature maps generated by the second encoder from the training input images from the second domain.

3. The method of claim 2, wherein the first encoder and the second encoder are trained such that the feature maps feature maps generated by the first encoder from training input images from the first domain have a similar distribution to the feature maps generated by the second encoder from the training input images from the second domain so that the feature maps generated by the first and second encoders become indistinguishable to the discriminator network.

4. The method of claim 2, wherein the first encoder for the first domain, the second encoder for the second domain, the decoder, and the discriminator network are trained together to iteratively learn parameters for the first encoder, the second encoder, the decoder, and the discriminator network to optimize a minimax objective function including a first term related to error between ground truth output images from the first domain and output images predicted from training input images from the first domain using the first encoder and the decoder, a second term related to error between ground truth output images from the second domain and output images predicted from training input images from the second domain using the second encoder and the decoder, a third term related to classification by the discriminator network of the feature maps generated by the first encoder from the training input images from the first domain, and a fourth term related to classification by the discriminator network of the feature maps generated by the second encoder from the training input images from the second domain.

5. The method of claim 2, further comprising:
 training, in a training stage prior to receiving the medical image of the patient, the first encoder, the second encoder, the decoder, and the discriminator network based on a first set of training samples including a plurality of training input images and corresponding ground truth output images from the first domain and a second set of training samples including a plurality training input images and corresponding ground truth output images from the second domain.

6. The method of claim 5, wherein training, in a training stage prior to receiving the medical image of the patient, the first encoder, the second encoder, the decoder, and the discriminator network based on a first set of training samples including a plurality of training input images and corresponding ground truth output images from the first domain and a second set of training samples including a plurality training input images and corresponding ground truth output images from the second domain comprises:

iterating training operations (a)-(d) for a plurality of iterations:
(a) with parameters of the first encoder and the second encoder fixed, learning parameters of the discriminator network to maximize positive classifications by the discriminator for the feature maps generated by the first encoder from the training input images from the first domain over the first set of training samples and negative classifications by the discriminator for the feature maps generated by the second encoder from the training input images from the second domain over the second set of training samples;
(b) with parameters of the first encoder and the second encoder fixed, learning parameters of the decoder that minimize error between the ground truth output images from the first domain and output images predicted from the training input images from the first domain using the first encoder and the decoder over the first set of training samples and error between the ground truth output images from the second domain and output images predicted from the training input images from the second domain using the second encoder and the decoder over the second set of training samples;
(c) with the parameters of the decoder and the discriminator network fixed, learning the parameters of the first encoder to minimize the error between the ground truth output images from the first domain and the output images predicted from the training input images from the first domain using the first encoder and the decoder and the positive classification by the discriminator for the feature maps generated by the first encoder from the training input images from the first domain over the first set of training samples; and
(d) with the parameters of the decoder and the discriminator network fixed, learning the parameters of the second encoder to minimize the error between the ground truth output images from the second domain and the output images predicted from the training input images from the second domain using the second encoder and the decoder and to maximize positive classifications by the discriminator for the feature maps generated by the second encoder from the training input images from the second domain over the second set of training samples.

7. The method of claim 6, wherein in each of the plurality of iterations, training operations (a) and (b) are performed in parallel and training operations (c) and (d) are performed in parallel.

8. The method of claim 1, further comprising:
receiving a second medical image from the second domain;
inputting the second medical image to the second encoder of the cross-domain deep-image to image network; and
automatically generating a second output image that provides a result of the target medical image analysis task on the second medical image using the cross-domain deep image-to-image network, by the second encoder converting the input second medical image from the second domain to a feature map and the decoder generating the second output image from the feature map generated by the second encoder.

9. An apparatus for automatically performing cross-domain based medical image analysis on a medical image of a patient, comprising:
a processor; and
a memory storing computer program instructions, which when executed by the processor cause the processor to perform operations comprising:
receiving a medical image of a patient from a first domain;
inputting the medical image of the patient to a first encoder of a cross-domain deep image-to-image network including the first encoder for the first domain, a second encoder for a second domain, and a decoder; and
automatically generating an output image that provides a result of a target medical image analysis task on the input medical image using the cross-domain deep image-to-image network, by the first encoder converting the input medical image from the first domain to a feature map and the decoder generating the output image from the feature map generated by the first encoder, wherein the first encoder for the first domain is trained together with the second encoder for the second domain at least in part based on a similarity of feature maps generated by the first encoder from training input images from the first domain and feature maps generated by the second encoder from training input images from the second domain, and the decoder is trained to generate output images from the feature maps generated by the first encoder and the feature maps generated by the second encoder.

10. The apparatus of claim 9, wherein the first encoder for the first domain, the second encoder for the second domain, and the decoder of the cross-domain deep image-to-image network are trained together in an adversarial network with a discriminator network for distinguishing between the feature maps generated by the first encoder from the training input images from the first domain and the feature maps generated by the second encoder from the training input images from the second domain.

11. The apparatus of claim 10, wherein the first encoder and the second encoder are trained such that the feature maps feature maps generated by the first encoder from training input images from the first domain have a similar distribution to the feature maps generated by the second encoder from the training input images from the second domain so that the feature maps generated by the first and second encoders become indistinguishable to the discriminator network.

12. The apparatus of claim 10, wherein the operations further comprise:
training the first encoder, the second encoder, the decoder, and the discriminator network based on a first set of training samples including a plurality of training input images and corresponding ground truth output images from the first domain and a second set of training samples including a plurality training input images and corresponding ground truth output images from the second domain, by iterating training operations (a)-(d) for a plurality of iterations:
(a) with parameters of the first encoder and the second encoder fixed, learning parameters of the discriminator network to maximize positive classifications by the discriminator for the feature maps generated by the first encoder from the training input images from the first domain over the first set of training samples and negative classifications by the discriminator for the feature maps generated by the second encoder from the training input images from the second domain over the second set of training samples;

(b) with parameters of the first encoder and the second encoder fixed, learning parameters of the decoder that minimize error between the ground truth output images from the first domain and output images predicted from the training input images from the first domain using the first encoder and the decoder over the first set of training samples and error between the ground truth output images from the second domain and output images predicted from the training input images from the second domain using the second encoder and the decoder over the second set of training samples;

(c) with the parameters of the decoder and the discriminator network fixed, learning the parameters of the first encoder to minimize the error between the ground truth output images from the first domain and the output images predicted from the training input images from the first domain using the first encoder and the decoder and the positive classification by the discriminator for the feature maps generated by the first encoder from the training input images from the first domain over the first set of training samples; and (d) with the parameters of the decoder and the discriminator network fixed, learning the parameters of the second encoder to minimize the error between the ground truth output images from the second domain and the output images predicted from the training input images from the second domain using the second encoder and the decoder and to maximize positive classifications by the discriminator for the feature maps generated by the second encoder from the training input images from the second domain over the second set of training samples.

13. The apparatus of claim 9, wherein the operations further comprise:

receiving a second medical image from the second domain;

inputting the second medical image to the second encoder of the cross-domain deep-image to image network; and automatically generating a second output image that provides a result of the target medical image analysis task on the second medical image using the cross-domain deep image-to-image network, by the second encoder converting the input second medical image from the second domain to a feature map and the decoder generating the second output image from the feature map generated by the second encoder.

* * * * *